US00PP29020P2

(12) United States Plant Patent
Danziger

(10) Patent No.: US PP29,020 P2
(45) Date of Patent: Feb. 27, 2018

(54) ***PETUNIA* PLANT NAMED 'DAMORQUEEN'**

(50) Latin Name: *Petunia hybrida*
Varietal Denomination: DAMORQUEEN

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 15/330,926

(22) Filed: Nov. 14, 2016

(51) Int. Cl.
*A01H 5/02* (2006.01)

(52) U.S. Cl.
USPC ..... Plt./356.13

(58) Field of Classification Search
USPC ..... Plt./263.1, 356.1, 356.13
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Petunia* cultivar named 'DAMORQUEEN' is disclosed, characterized by well-branched plants with a mounded growth habit and medium vigor. Plants flower abundantly and produce large flowers. Flower color is uniquely red with yellow stripes, which can appear as heart shapes along margin with high light conditions. The new variety is a *Petunia*, suitable as an outdoor garden or container plant.

3 Drawing Sheets

Latin name of the genus and species: *Petunia hybrida*.

Variety denomination: 'DAMORQUEEN'.

The new *Petunia* cultivar resulted as part of a planned breeding program by the inventor Gavriel Danziger. The objective of the breeding program was to develop new *Petunia* varieties with interesting color patterns and attractive plant forms.

The new variety resulted from a controlled crossing of the seed parent, an unpatented, proprietary seedling referred to as 'c.v. 12-6708' with the pollen parent, an unpatented, proprietary seedling referred to as 'c.v.12-6237'. The crossing was made at a research greenhouse in Israel during January of 2014. The new variety was discovered in September 2014 by the inventor in a group of seedlings resulting from the January crossing in a research greenhouse in Moshav Mishmar Hashiva, Israel.

Asexual reproduction of the new cultivar 'DAMORQUEEN' by vegetative cuttings was first performed at a greenhouse as well as outdoors in Moshav Mishmar Hashiva, Israel in October 2014. Subsequent propagation by vegetative cuttings has shown that the unique features of this cultivar are stable and reproduced true to type in several successive generations.

SUMMARY OF THE INVENTION

The cultivar 'DAMORQUEEN' has not observed under all possible environmental conditions. The phenotype may vary somewhat with variations in environment such as temperature, day length and light intensity, without however, any variance in genotype.

The following traits have been repeatedly observed and are determined to be the unique characteristics of 'DAMORQUEEN'. These characteristics in combination distinguish 'DAMORQUEEN' as a new and distinct *Petunia* cultivar:

1. Mounded growth habit.
2. Very well branched plant with medium vigor.

3. Flowers color is red with yellow stripes. Higher light intensity influences the configuration of the stripes. Higher light intensity increase the size of the yellow striping, resulting in a heart-shaped pattern along the margin of the flower.
4. Large flower size.
5. Abundant flowering.

COMPARISON TO THE PARENT VARIETY

Plants of the new cultivar are similar to plants of the seed parent, most horticultural characteristics, however, plants of the new cultivar differ in the following;

1. The seed parent variety is a semi-upright plant, the new variety is mounding.
2. The seed parent variety is more compact and not very well-branched.
3. The seed parent flower color is white with red stripes, the new variety is red with yellow stripes.
4. Flowers of the seed parent are larger.
5. The new variety flowers more abundantly.

Plants of the new cultivar are similar to plants of the pollen parent, most horticultural characteristics, however, plants of the new cultivar differ in the following;

1. Plants of the pollen parent are larger and more vigorous than plants of the new variety.
4. Flowers size of the pollen parent is medium, flower size of the new variety is large.
5. Plants of the new variety flowering more abundantly than plants of the pollen parent.

COMPARISON TO COMMERCIAL VARIETIES

Plants of the new cultivar can be compared to the unpatented commercial variety *Petunia* 'Dancas305'. These varieties are similar in most horticultural characteristics; however, the new cultivar differs in the following:

1. Comparator flower size is smaller than the flower of the new variety.
2. Comparator flower color is purple with white stripes, while the new variety has red flower with yellow stripes.
3. Comparator plant habit is semi-trailing, while the new variety has a mounded growth habit.

Plants of the new cultivar can be compared to the patented commercial variety *Petunia* 'DRAY67', U.S. Plant Pat. No. 25,906. These varieties are similar in most horticultural characteristics; however, the new cultivar differs in the following:

1. Comparator flower size is smaller than the flower of the new variety.
2. Comparator flower color is black with yellow stripes, while the new variety has red flowers with yellow stripes.
3. Comparator plant is taller than plants of the new variety.

BRIEF DESCRIPTION OF THE PHOTOGRAPHS

The accompanying photograph in FIG. 1 illustrates in full color a typical plant of 'DAMORQUEEN' grown in a greenhouse, in a 10 inch commercial basket. Age of the plant photographed is approximately 20 weeks from 5 rooted cuttings. The plant in FIG. 1 has been grown under high light conditions, photographed during May.

Figure 1:
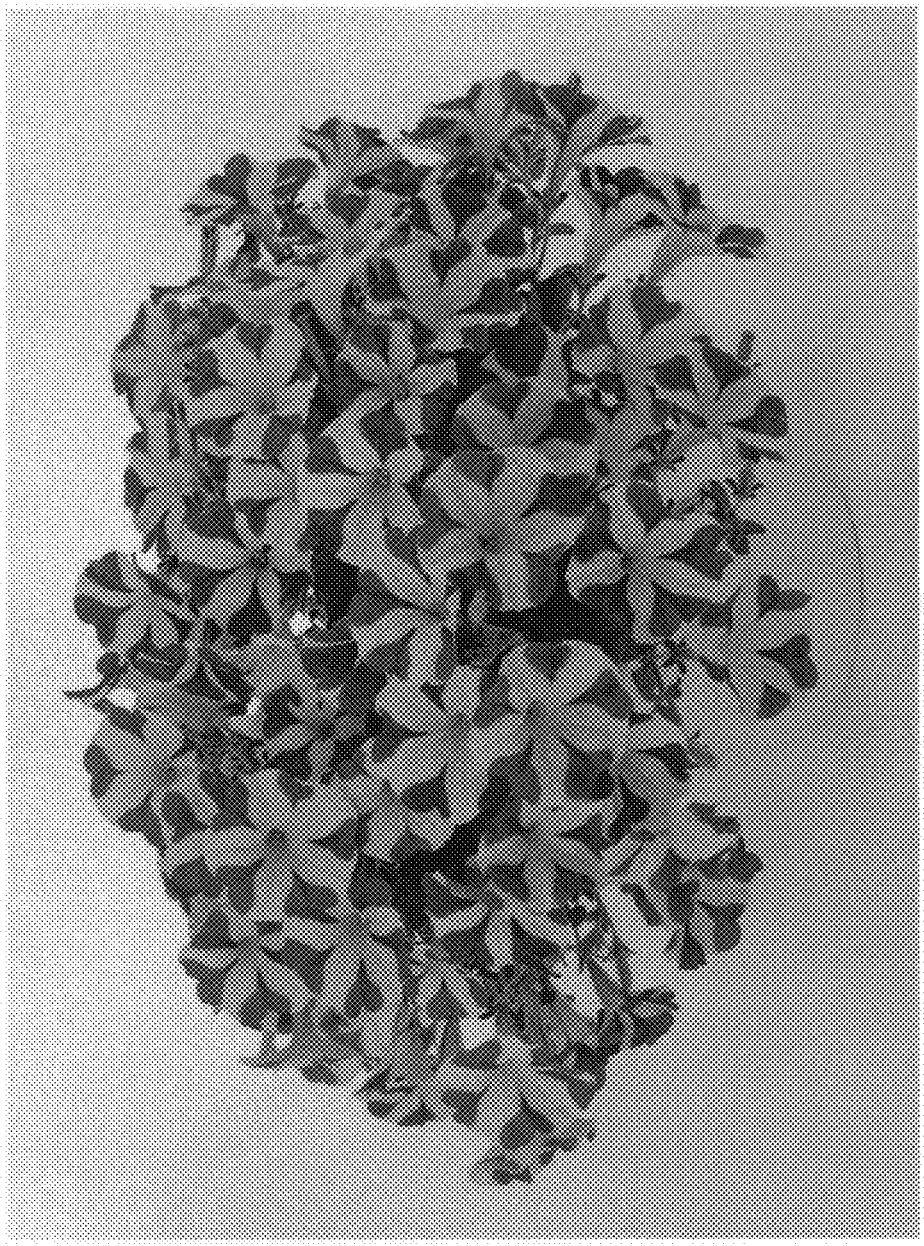
Figure 2:
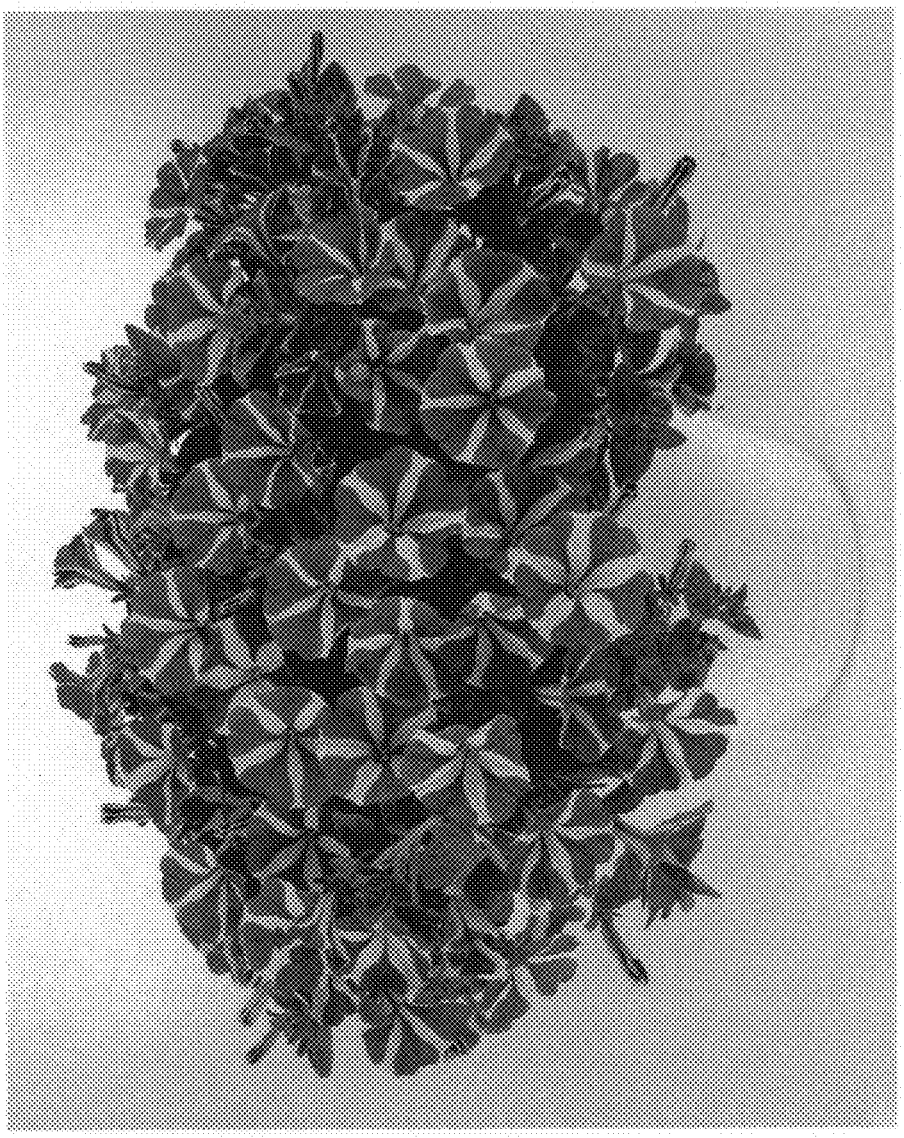
FIG. 2 illustrates a similar aged plant, in a 10 inch commercial basket. The plant in FIG. 2 was grown under lower light conditions, and photographed 4 to 6 weeks earlier in Spring.
Figure 3:
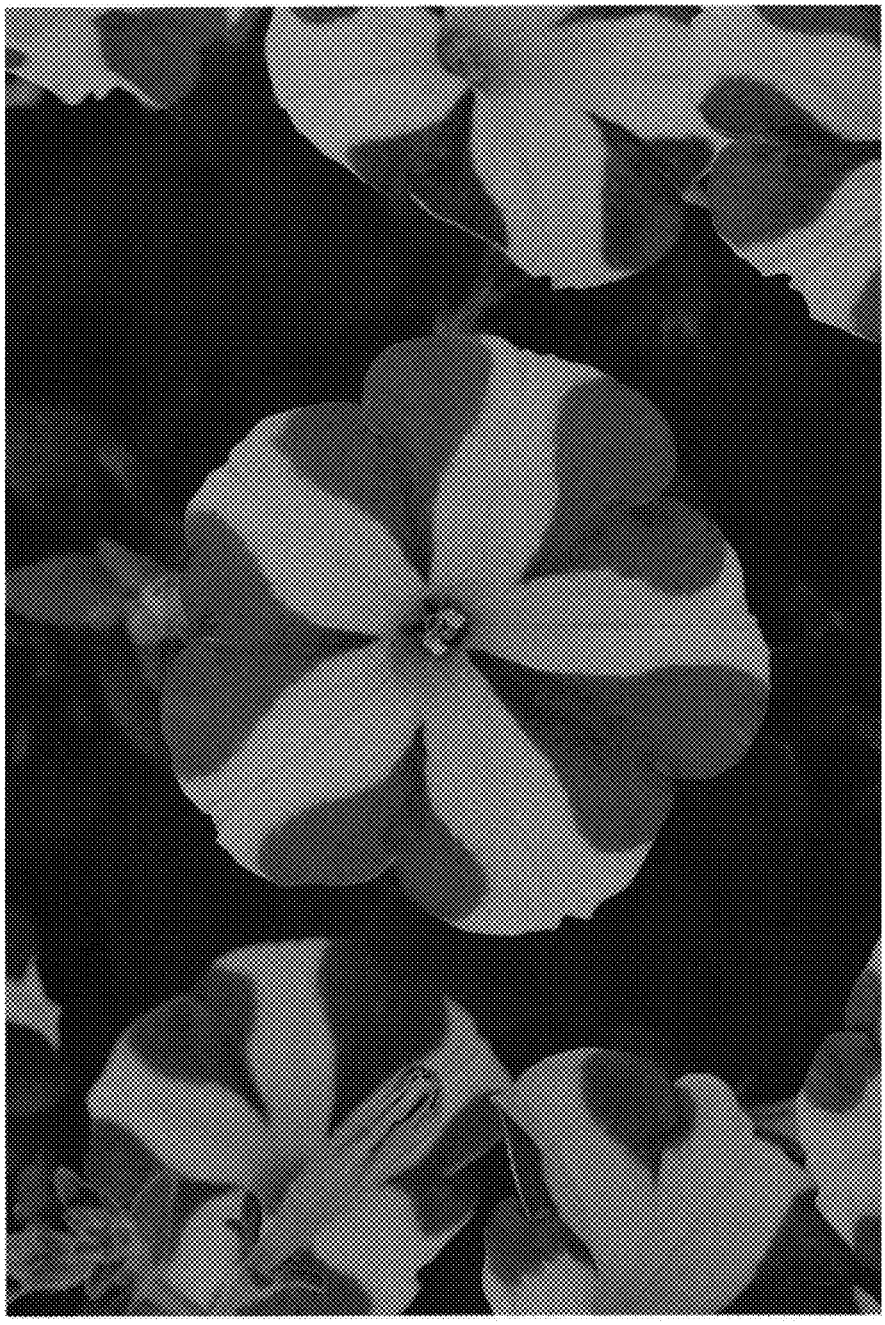
FIG. 3 illustrates a close up view of the flowers, grown under high light conditions.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurement describe 'DAMORQUEEN' plants grown in a greenhouse and outdoors in Moshav Mishmar Harshiva, Israel during the Spring. The growing temperature ranged from 20° C. to 35° C. day 17° C. to 23° C. night. General light conditions are bright, normal sunlight with some shade during the brightest part of the day. Measurements and numerical values represent averages of typical plant types. Botanical classification: *Petunia hybrida.*

PROPAGATION

Time to initiate roots: About 10 to 14 days at approximately 20° C.

Root description: Fibrous. Tan to brown, not accurately measured with R.H.S. chart.

PLANT

Growth habit: Mounded.

Pot size of plant described: 13 cm.

Height: To top of flowers: About 20 cm.

Plant spread: About 50 cm.

Growth rate: Medium.

Branching characteristics: Very well branched.

Length of primary lateral branches: About 25 cm.

Quantity of primary lateral branches: 8.

Characteristics of primary lateral branches:

*Form.*—Cylindrical.

*Diameter.*—About 0.3 cm.

*Color.*—RHS Yellow-Green 144 B.

*Texture.*—Pubescent.

*Strength.*—Good.

Internode length: About 1.5 cm.

FOLIAGE

Leaf:

*Arrangement.*—Opposite.

*Quantity.*—Approximately 25 per branch.

*Average length.*—5.0 cm.

*Average width.*—2.5 cm.

*Shape of blade.*—Elliptic.

*Apex.*—Acute.

*Base.*—Attenuate.

*Margin.*—Entire.

*Texture of top surface.*—Velvety.

*Texture of bottom surface.*—Velvety.

*Color.*—Young foliage upper side: RHS Green 137 B. Young foliage under side: RHS Green 137 C. Mature foliage upper side: RHS Green 137 A. Mature foliage under side: RIIS Green 137 C.

*Venation.*—Type: Pinnate. Venation color upper side: RHS Green 137 C. Venation color under side: RHS 137 D.

*Petiole.*—Length: About 0.5 cm. Diameter: About 0.3 cm. Color: RHS Green 137 A. Texture: Velvety.

FLOWER

Natural flowering season: Spring, summer, and autumn, under environmental conditions similar to Israel.

Days to flowering from rooted cutting: Approximately 30 days.

Inflorescence and flower type and habit: Axillary, single flower, salverform shape, erect habit.

Rate of flower opening: Approximately 2 to 3 days from bud to fully opened flower.

Flower longevity on plant: Approximately 3 to 6 days.

Approximate quantity of flowers per plant: Approximately 60.

Flowers persistent or self-cleaning: Self-cleaning.

Bud:

*Shape.*—Tubular.

*Length.*—Approximately 4.0 cm.

*Diameter.*—Approximately 0.8 cm.

*Color.*—RHS Yellow-green 154 C with Stripes Red-Purple 60 A.

Flower size:

*Diameter.*—6 cm.

*Flower tube length.*—About 2.5 cm.

*Flower tube diameter at distal end.*—About 1.2 cm.

*Flower tube diameter at proximal end.*—0.3 cm.

Petals:

*Length from throat.*—About 2.5 cm.

*Width.*—Approximately 2.5 cm.

*Quantity.*—5.

*Texture.*—Velvety.

*Apex*.—Blunt, with shallow lobes or notches.
*Margin*.—Entire.

Color:
*When opening*.—Upper surface: RHS Red-Purple 59 A with 5 Stripes, Yellow 4 A. Lower surface: RHS Red-Purple 60 C with 5 Stripes, Yellow 4 B.
*Fully opened*.—Upper surface: RHS Red-Purple 60 A with 5 Stripes, Yellow 8 A. Lower surface: Red-Purple 60 C with 5 Stripes, Yellow 8 B. Flower throat (inside): RHS Red-Purple 59 A with 5 Stripes, Yellow 4 A. Flower throat, vein: RHS Yellow 4 A. Flower tube (outside): RHS Red-Purple 60 C with 5 Stripes, Yellow 8 B. Flower tube, vein: RHS Yellow 4 A.
*Fading*.—Petals fading to: RHS Red-Purple 60 C with 5 Stripes, Yellow 4 C.

Calyx/sepals:
*Quantity per flower*.—5.
*Shape*.—Linear.
*Length*.—About 2 cm.
*Width*.—About 0.4 cm.
*Apex*.—Acute.
*Base*.—Cuneate.
*Margin*.—Entire.
*Texture*.—Velvety.
*Color*.—Upper Surface: RHS Green 137 A. Lower Surface: RHS Green 137 C.

Pedicel:
*Length*.—About 2.5 cm.
*Diameter*.—About 0.2 cm.
*Color*.—RHS Yellow-Green 146 B.
*Orientation*.—45 degrees.

Fragrance: None.

REPRODUCTIVE ORGANS

Stamens:
*Number*.—5.
*Filament length*.—About 2 cm.

Anthers:
*Length*.—About 0.1 cm.
*Shape*.—Rounded.
*Color*.—RHS yellow 9 C.
*Pollen*.—Color: RHS Yellow 9 D. Quantity: Abundant.

Pistil:
*Number*.—1.
*Length*.—About 2.0 cm.
*Style*.—Length: about 1.5 cm. Color: RHS Yellow-Green 154 C.
*Stigma*.—Shape: Rounded. Color: RHS Green 143 C. Ovary Color: RHS Green 144 B.

OTHER CHARACTERISTICS

Seeds and fruits:
*Quantity*.—About 50 brown, rounded seeds of about 0.5 mm diameter, per one brown, conical capsule.

Disease/pest resistance: Neither resistance nor susceptibility to the normal diseases and pest of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Typical range from 5° to 40° C.

What is claimed is:

1. A new and distinct cultivar of *Petunia* plant named 'DAMORQUEEN' as herein illustrated and described.

* * * * *